United States Patent
Kaufman (10) Patent No.: US 7,288,414 B2
(45) Date of Patent: Oct. 30, 2007

(54) USE OF PHOSPHONAZO III FOR THE MEASUREMENT OF CALCIUM, MAGNESIUM AND SODIUM IN ANALYTICAL SAMPLES

(75) Inventor: Richard A. Kaufman, Bound Brook, NJ (US)

(73) Assignee: Specialty Assays, Inc., Hillsburough, NJ (US)

( * ) Notice: Subject to any disclaimer, the term of this patent is extended or adjusted under 35 U.S.C. 154(b) by 206 days.

(21) Appl. No.: 11/109,083

(22) Filed: Apr. 19, 2005

(65) Prior Publication Data
US 2006/0234384 A1    Oct. 19, 2006

(51) Int. Cl.
*G01N 33/20* (2006.01)

(52) U.S. Cl. .......... 436/79; 422/61; 422/68.1; 422/82.05; 436/43; 436/73; 436/166

(58) Field of Classification Search ........... 422/61, 422/68.1, 82.05; 436/43, 73, 79, 164, 166
See application file for complete search history.

(56) References Cited

U.S. PATENT DOCUMENTS 3,934,977 A * 1/1976 Cleaver .............. 436/74

5,482,866 A * 1/1996 Denton et al. .......... 436/79
5,592,290 A * 1/1997 Arai et al. .............. 356/300

FOREIGN PATENT DOCUMENTS

| EP | 308670 | * | 3/1989 |
| GB | 1123094 | * | 8/1968 |
| GB | 2002514 | * | 2/1979 |

OTHER PUBLICATIONS

Ferguson J. W. et al, Analytical Chemistry 1964, 36, 796-799.*
Luk'yanov, V. F. et al, Chemical Abstracts 1971, 75, abstract 29598.*
Zenki, M., Analytica Chimica Acta 197), 93, 323-326.*
Kaneko, K. et al, Analytica Chimica Acta 1981, 132, 165-173.*
Yuan, Y., Analytica Chimica Acta 1988, 212, 291-295.*
Wada, H. et al, Journal of Chromatography 1993, 657, 87-93.*
Budesinsky, B. et al, Collection of Czechoslovak Chemical Communications 1967, 32, 1528-1540.*
Luk'yanov, V. F. et al, Zhurnal Analiticheskoi Khimii 1971, 26, 772-766.*
Durham, A. C. H. et al, Cell Calcium 1983, 4, 47-55.*
Gao, H.-W., Journal of Analytical Chemistry 1997, 52, 141-143.*
Yu, J. et al, Shandong Jiancai Xueyuan Xuebao 2000, 14, 163-164.*

* cited by examiner

*Primary Examiner*—Arlen Soderquist
(74) *Attorney, Agent, or Firm*—Lucas & Mercanti, LLP (57) ABSTRACT

Novel reagent formulations and methods are described for the use of phosphonazo III to measure calcium, magnesium and sodium in biological fluids.

22 Claims, 2 Drawing Sheets

Buffer: 0.05 mol/L DIPSO, pH 7.0
Phosphonazo III concentration = 62 umol/L
Calcium concentration = 20 umol/L
Magnesium concentration = 20 umol/L
Pathlength 1 cm

Sodium Concentration = 930 umol/L
Phosphonazo III Concentration = 200 umol/L
Buffer = 9.5 mmol/L Diethylenetriaminepentaacetic acid-Triethylamine pH 8.5 containing 48% Dimethylsulfoxide and 14.3% D-Glucose continued from previous text …

USE OF PHOSPHONAZO III FOR THE MEASUREMENT OF CALCIUM, MAGNESIUM AND SODIUM IN ANALYTICAL SAMPLES

TECHNICAL FIELD

The invention is directed to a method for quantitating calcium, magnesium and sodium in analytical samples using phosphonazo III as well as novel reagent compositions used therein.

BACKGROUND OF THE INVENTION

Calcium is the fifth most common element in the body where 99% exists in the bones as crystalline hydroxyapatite. The extracellular fluids contain about 0.1% of the total body calcium and of the extracellular fluids, about 30% exists in the blood plasma.

The physiological functions of calcium are diverse. Intracellularly calcium modulates the activities of several enzymes, most notably adenylate cyclase and calmodulin. It is also involved in the regulation of a multitude of cellular functions including fertilization, mitosis, cell motility and ancillary action. In striated muscle, calcium activates contraction of the musin fibrils through combination with troponin a calcium binding protein. Calcium also serves to regulate membrane permeability, causes neurotransmitter release and diminishes neuromuscular excitability. For an in-depth discussion of calcium metabolism and function see Fundamentals of Clinical Chemistry, $3^{rd}$ ed., Editor Norbert W. Tietz, W. B. Saunders Co. (1987).

Clinically, serum calcium levels are of significant diagnostic value. The reference range is very narrow, 2.20 to 2.55 mmol/L, and slight deviations above or below these levels are diagnostic of several physiological disorders. The two most common diseases associated with hypercalcemia (elevated serum calcium) are hyperparathyroidism and malignancy, especially when the malignancy has metastasized to the skeleton and caused bone destruction. Decreased serum calcium levels (hypocalcemia) is commonly associated with hypoparathyroidism. In newborn infants about 1% have significant hypocalcemia (serum calcium <1.75 mmol/L) and exhibit symptoms of hypocalcemia which include irritability, twitching and convulsions which require immediate medical intervention.

Magnesium, like calcium, is one of the major elements found in the body. A typical 70 kg human adult contains about 20 to 28 g of magnesium of which about 55% is found in the bones and 27% in the muscles. The serum reference range of magnesium is also rather narrow being from 0.65 to 1.05 mmol/L. Low levels of serum magnesium, hypomagnesemia (<0.5 mmol/L) is manifested by impairment of neuromuscular function which leads to hyperirritability, tetany and convulsions, symptoms which are nearly identical to hypocalcemia. Increased serum magnesium levels have a sedative effect on the body.

Given the nearly identical clinical symptoms of low serum calcium and low serum magnesium, it is imperative to delineate which element is causing the clinical symptoms. Often both serum calcium and magnesium measurements are necessary to determine which element or if both elements are low.

The reference method for measuring calcium and magnesium is atomic absorption. The technique is nearly interference free, requires a small sample volume and gives good precision and reproducibility. For routine measurements, atomic absorption is somewhat inconvenient, requires expensive instrumentation and a rather skilled operator to perform assays.

Present methodologies in routine use in clinical laboratories for measuring calcium use procedures based on ortho-cresolphthalein complexone (CPC) and arsenazo III. Although both methods are in wide use, each is not without its drawbacks. The sensitivity of CPC methods is very dependent on pH. For maximum sensitivity the reaction is carried out at a pH of about 11.7. At these alkaline pH values, however, the reagent readily absorbs ambient carbon dioxide which combines with water to form carbonic acid which gradually reduces the reagent pH and eventually renders the reagent non-functional for calcium measurements. Also, CPC is rather non-selective and binds magnesium and other heavy metals. To eliminate magnesium interference at the levels normally encountered in serum, 8-hydroxyquinoline is added to chelate magnesium, but this compound also chelates calcium and decreases the sensitivity by 25 to 40%. Arsenazo III methods do not suffer from the problems of high pH and magnesium interference (depending on measurement pH) inherent in the CPC methods. It binds calcium under weakly acidic conditions, e.g. pH 5 to 6, and if the calcium measurement is made at a pH less than 7, binding of magnesium is negligible. Although arsenazo III eliminates many of the disadvantages of CPC methods, it suffers from rather low sensitivity and environmental concerns. Each mole of arsenazo III contains 2 moles of arsenic, and disposal of the arsenazo III reagents is becoming a serious issue in many countries due to concerns of contamination of the water supply with arsenic.

Tanaka, et al. (U.S. Pat. No. 4,966,784) and Kaufman et al. (U.S. Pat. No. 5,589,348) have developed methods for measuring calcium using chlorophosphonazo III. Although this chromophore does not contain arsenic, it tends to have relatively a high reagent blank absorbance which limits the linearity for calcium on many analyzers. Chapoteau et al. have developed calcium methods using phenolic derivatives of tetraacetic acid (U.S. Pat. No. 5,262,330). However, to bind calcium the assays still require an alkaline pH.

The problems plaguing calcium assays are also common to magnesium assays. Calmagite methods (U.S. Pat. No. 4,383,043) are routinely used by many clinical laboratories, and other methods have been developed using Xylidyl Blue, Xylazo Violet I and II (U.S. Pat. No. 4,503,156), and Erichrome Black T (U.S. Pat. No. 4,383,043). As with calcium assays, all the preceding magnesium methods require a high pH (>>9) and pH stability of the reagent in an uncapped vial is limited due to absorption of ambient carbon dioxide. A recent method for measuring magnesium was published using chlorophosphonazo III (U.S. Pat. Nos. 5,589,348 and 5,397,710). Although this chromophore overcomes the high pH requirement to bind magnesium, it still suffers from a relatively high reagent blank absorbance which limits the linearity for magnesium on many clinical chemistry analyzers used in clinical laboratories.

Thus, there are unmet needs for methods to quantitatively measure calcium and magnesium in analytical samples. The method should a) bind calcium and magnesium around a neutral or slightly acidic pH, b) the chromophore should contain no toxic elements e.g. arsenic, c) the chromophore should have a relatively low reagent blank absorbance, and d) the reagent should have safe handling characteristics, e.g. a pH around neutrality, in case of skin contact or spillage.

Sodium is by far the most prevalent cation in the extracellular fluid and in plasma and serum. The main function of sodium in the body is to maintain the normal distribution of water and the osmotic pressure in the extracellular compartment.

Sodium in body fluids, e.g. serum and plasma, is typically measured by either flame emission spectroscopy or sodium ion specific electrodes. Although both methods generally work quite well each is not without its drawbacks. In the United States, OSHA (Occupational Safety and Health Administration) has dictated flame photometers use propane as the fuel. Propane gas leaks can readily occur from tanks, valves and fittings and discharge propane into the work area thus posing a potential explosion hazard. Also flame characteristics may change as the propane tanks reach exhaustion and this may require more frequent calibration or a flame that has unusable characteristics.

Sodium ion specific electrodes overcome the safety issues with flame photometry. Although the electrodes generally work well, they need frequent cleaning to remove protein build-up and they have a finite working lifetime and electrode replacement cost is somewhat expensive. Also the initial cost of the instrumentation to run the electrodes on is prohibitive for many small clinical laboratories.

Some attempts have been made to measure sodium colorimetrically. Chapoteau et al. (U.S. Pat. No. 4,808,539) and Cram et al. (U.S. Pat. No. 5,011,924) have respectively developed procedures using "chromogenic cryptands" and "chromogenic cryptahemispherands" to measure sodium in serum. Also a kinetic enzymatic procedure was published by Berry et al. (Clin. Chem. 34, 2295-2298 (1988)) using the enzyme beta-galactosidase where the enzyme activity was activated in the presence of low concentrations of sodium.

In 1966 Budesinsky et. al. (Tschechoslow. Pat. Nr. 122379) described the synthesis of a series of chromotroptic acid derivatives including phosphonazo III and presented spectral data of chelates of several heavy metals and transition metal ions (Coll. Czech. Chem. Comm. 32, 1967 and Talanta 15(10), 1063-4, 1968). A summary of the data was later published in *Chelates in Analytical Chemistry*, 1969, Vol. 2, Marcel Dekker Inc., New York, N.Y. (p1-91). About the same time, a group of Russian scientists presented spectral data of phosphonazo III and other derivatives with several divalent and transition metal ions (Luken et al. Dokl, Akad. Nauk. SSSR 173(2), 361-363, 1967) and other investigators demonstrated the complexation and spectral properties of several rare earth metals with phosphonazo III (Zh. Anal. Khim., 26(4), J, 772-6, 1971; Zh. Anal. Khim. 32(4), 674-678, 1997; and Tr. Vses. Nauch.-Issled. Inst. Khim. Reaktivov Osobo Chist. Khim. Veshchesestv, 1967, No. 30, 42-9).

SUMMARY OF THE INVENTION

In accordance with one aspect of the invention, there is provided a diagnostic reagent kit useful for the measurement of calcium, magnesium or sodium, for example. The kit includes a compound of Formula (I):

wherein $R_1$-$R_8$ are independently selected from among H, $C_{1-6}$ alkyls, $C_{1-6}$ etheralkyls, $C_{3-6}$ branched alkyls, $C_{3-8}$ cycloalkyls and halogens. In many preferred aspects of the invention, $R_1$-$R_8$ are all H so that the compound included in the kit is phosphonazo III, structure shown below In another preferred aspect of the invention, there are provided methods for quantitatively determining the concentration of calcium, magnesium or sodium in an analytical sample. The methods include:

a) contacting a sample with a compound of Formula (I) such as phosphonazo III; and b) measuring the change in absorbance, reflectance or fluorescence resulting from said contacting step a).

In an alternative aspect of the invention, the method include the steps of:

a) measuring the absorbance, reflectance or fluorescence of a reagent containing a compound of Formula (I), i.e. phosphonazo III, (reagent blank);

b) adding a sample to the reagent;

c) measuring the absorbance, reflectance or fluorescence after adding the sample to the reagent; and d) subtracting the absorbance, reflectance or fluorescence measurement obtained from step a) from that obtained as a result of step c) to obtain the net absorbance, reflectance or fluorescence due to the calcium, magnesium or sodium in the sample.

In still further aspects of the invention, there are provided kits useful for the measurement of sodium and methods for quantitatively determining the concentration of sodium in an analytical sample. In each of these aspects, the kits and methods include a compound of formula (I) where $R_3$ and $R_7$ are Cl.

One of the advantages of the present invention is that the preferred compound of Formula (I), phosphonazo III, binds calcium over a wide range of pH, from about 2 to 11. The pH of maximum sensitivity is at about pH 7. Thus reagent solutions prepared in buffers at pH 7 or slightly acidic pH values will not be affected by ambient carbon dioxide absorption by the reagent and thus less waste will be encountered by not having to discard deteriorated reagent. Phosphonazo III also binds magnesium over the pH range of about 6 to 11 with a pH for maximum sensitivity of about 7. Thus, as with calcium, reagent solutions for magnesium will not have their pH affected by absorption of ambient carbon dioxide. Phosphonazo III also binds sodium over a pH range of about 6 to 11 with a maximum sensitivity of about 9.

Another advantage of the invention is that phosphonazo III, see formula I above, contains no toxic elements as in the case of arsenazo III which contains 2 moles of arsenic. Thus, disposal of used reagent will not pose as great a toxicological problem as with arsenazo III.

In still another advantage of reagent kits and methods using phosphonazo III, the reagent blank absorbances in the assay for magnesium were found to be somewhat lower than with chlorophosphonazo III for measuring magnesium. Thus, linearity of magnesium tests will not be compromised due to absorbances being too high for some clinical chemistry analyzers to measure.

Reagent kits for calcium and magnesium can be prepared at near pH 7 which minimizes injuries from skin contact with the reagents and spillage.

The measurement of sodium, especially in serum, can be complicated by the presence of lipids which cause the samples to be turbid and the presence of hemoglobin and bilirubin have absorb in the visible region of the spectrum from about 440 to 575 nm. With phosphonazo III, the wavelength for maximum sensitivities of the sodium-phosphonazo III complex occurs at about 650 nm where spectral interference from hemoglobin and bilirubin is non-existent and interference from turbidity is minimal. This is a significant improvement compared with the shorter wavelengths, e.g. 500 and 405 nm respectively, in procedures used previously [Chapoteau et al. (U.S. Pat. No. 4,808,539) and Cram et al. (U.S. Pat. No. 5,011,924)] and Berry et al. (Clin. Chem. 34, 2295-2298 (1988)).

The use of phosphonazo III as an analytical reagent for quantitatively measuring calcium, magnesium and sodium in analytical samples, especially biological samples, was investigated and found to have several properties which overcome many of the shortcomings of present methods for measuring calcium, magnesium and sodium.

DETAILED DESCRIPTION OF THE INVENTION

One of the preferred compounds of formula (I), phosphonazo III was synthesized by Specialty Assays Inc., Manville, N.J., using various procedures throughout the literature such as *Chelates in Analytical Chemistry*, 1969, Vol. 2, Marcel Dekker Inc., New York, N.Y., p1-91 and J.O.C. 2450 (1964), the disclosure of which is incorporated herein by reference. Briefly, the procedure was as follows:

1. Diazotized ortho-chloroaniline was reacted with phosphorus trichloride to form ortho-chlorophenyl phosphine.
2. After hydrolysis of the phosphine the ortho-chlorophenylphosphonic acid was reacted with ammonia to form ortho-aminophenylphosphonic acid.
3. Two moles ortho-aminophenylphosphonic acid were diazotized and reacted with one mole chromotropic acid to form phosphonazo III.

Alternative compounds in accordance Formula (I) can also be synthesized using published techniques known to those of ordinary skill or are available, i.e. chlorphophonazo III, from suppliers. Simply by way of illustration and not limitation, the methyl, methoxy or ethoxy derivatives of Phosphonazo III can be prepared by the above procedure. For example, to prepare para-methylphosphonazo III one would substitute in step 1 above 2-chloro-5-methylaniline in place of ortho-chloroaniline. Similarly to prepare para-methoxyphosphonazo III one would substitute 5-chloro-o-anisidine in place of ortho-chloroaniline.

The invention is first directed to reagent compositions useful in the determination of calcium, magnesium and sodium in analytical samples. The determination of calcium, magnesium and sodium can be made using a one or two reagent system. The choice will depend on the preference of the artisan, but for biological samples which contain interfering spectral chromophores such as bilirubin, hemoglobin and lipemia, a two vial system may be preferred to correct for these spectral interferences. Phosphonazo III was found to bind calcium over a wide range pH range, from 2 to 11. However, at acidic pH values e.g. 2 to 6.5 calcium binding is enhanced relative to magnesium binding. For example, at pH 5.8, the sensitivity of magnesium is only about $\frac{1}{10}$ the sensitivity for calcium, while at pH 7 the sensitivity of magnesium is about 1.2 times that of calcium. Thus, to have minimal interference from magnesium when measuring calcium, it is preferable to carry out the assay at a pH below 7 or more preferably below 6. To have an assay substantially free from magnesium interference, a chelator may be added to complex magnesium and render it unavailable to react with phosphonazo III. Suitable chelators, include but are not limited to the following, were found to be useful for chelating magnesium: compounds containing one carboxylic acid group, a phosphoric acid group and dicarboxylic acid groups. Preferred chelators from these groups were the compounds malonic acid, oxalic acid, succinic acid, phthalic acid, tartaric acid, phenylphosphonic acid, malonic acid salt, oxalic acid salt, with malonic acid and oxalic acid being the most preferred. Concentrations of magnesium chelators will vary depending on the ratio of calcium to magnesium in the sample, but generally chelator concentrations from about 3 mmol/L to 150 mmol/L are suitable for most clinical applications. If a pH higher than 7 is used, additional chelators such as 8-hydroxyquinoline can be used. Examples of suitable buffers include but are not limited to:

Bis-Tris [Bis(2-hydroxyethyl)imino-tris(hydroxymethyl) methane],
MES [2-(N-Morpholino)ethanesulfonic acid],
BES [N,N-bis(Hydroxyethyl)-2-aminoethanesulfonic acid],
DIPSO [3-(N,N-Bis(hydroxyethyl)amino)-2-hydroxypropanesulfonic acid],
MOPS 3-(N-Morpholino)-propanesulfonic acid,
MOPSO 3-(N-Morpholino)-2-hydroxypropanesulfonic acid,
Imidazole,
TES N-Tris(Hydroxymethyl)methyl-2-aminoethanesulfonic acid,
ADA N-(2-Acetamido)-iminodiacetic acid,
ACES N-(2-Acetamido)-2-aminoethanesulfonic acid, and
TAPSO N-[Tris(hydroxymethyl)methyl]-3-amino-2-hydroxypropanesulfonic acid.

Other buffers would be useable as long as they have enough buffering capacity to the maintain the desired pH. Suitable buffer concentrations would be from about 0.01 to about 1 mol/L. In certain embodiments of the invention, the chelators mentioned above function as a buffer so that additional chelators can be eliminated, if desired.

Figure 1:
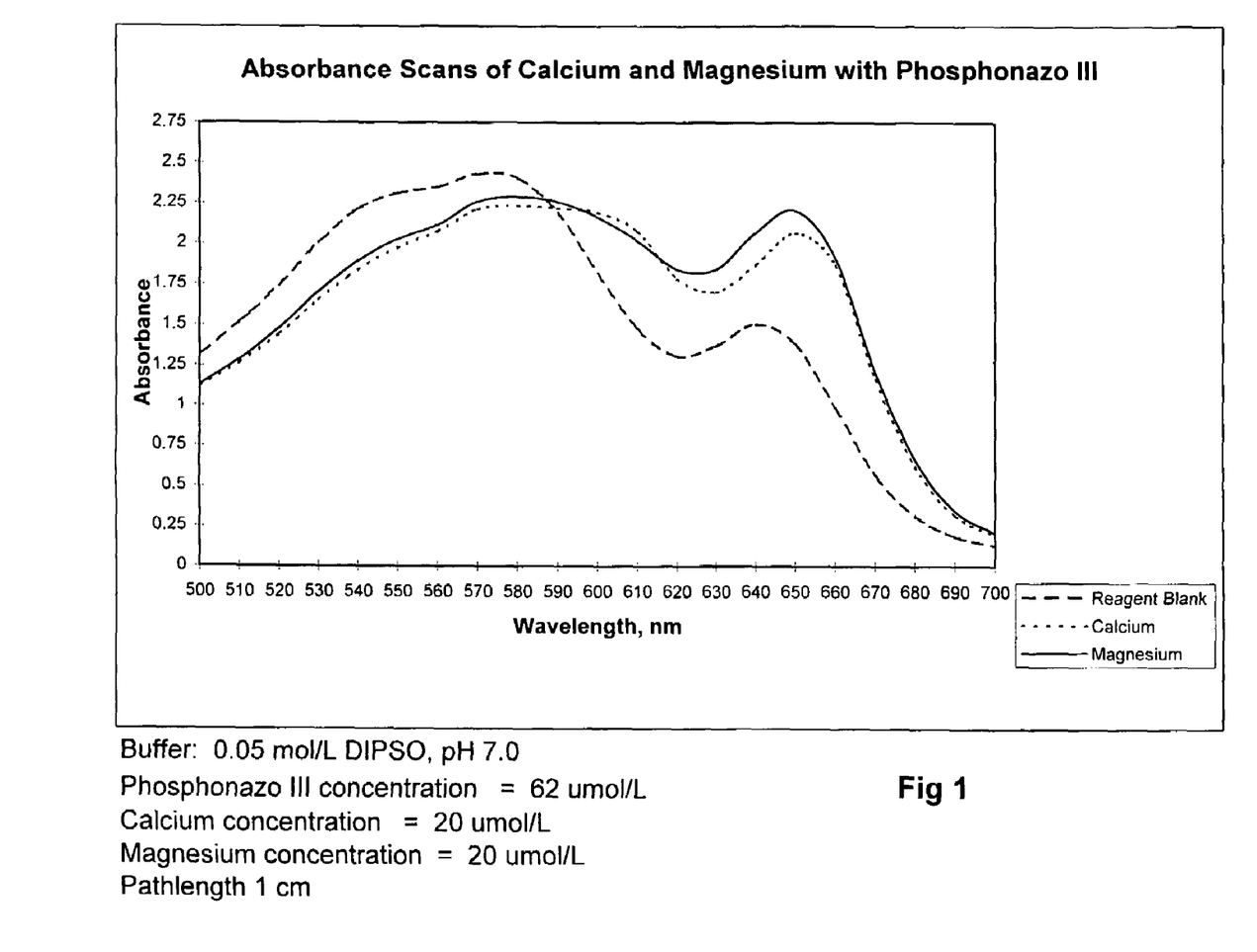
FIG. 1 shows absorbance spectra of phosphonazo III, Ca-phosphonazo III complex and Mg-phosphonazo III complex in 0.05 mol/L DIPSO buffer, pH 7.0. The phosphonazo III, calcium and magnesium concentrations are respectively 62, 20 and 20 umol/L.

As apparent from FIG. 1, the calcium-phosphonazo III complex exhibits absorption maxima in the visible region of spectrum. Virtually any wavelength can be used from 500 to 700 nm except the isosbectric point near 580 nm.

For magnesium assays, a pH of about 7 gives maximum sensitivity. Below pH about 6.5 binding of magnesium by phosphonazo III is significantly reduced and a pH values >>7, the reagent blank is increased significantly. At about pH 7, however, phosphonazo III also binds calcium and therefore a calcium chelator needs to be added, especially when significant amounts of calcium are present in the samples. Preferably, the calcium chelator should not bind significant quantities of magnesium when phosphonazo III is present. EGTA was found to be a suitable calcium chelator which virtually binds no magnesium at pH 7 in the presence of phosphonazo III. Suitable concentrations would be about 1 to 100 mmol/L. Also at a pH of about 7 and higher, phosphonazo III was found to slightly bind sodium in aqueous solutions. Thus a physiological concentration of sodium chloride would need to added to magnesium standards to correct for the slight interference or a suitable sodium chelator such as Kryptofix 221 (4,7,13,16,21-pentaoxa-1,10diazabicyclo[8.8.5]tricosane) could be added to the reagent. The choice of wavelengths to use for measuring the magnesium-phosphonazo III chelate is nearly identical to that for calcium. Any wavelength between 500 and 700 nm can used except for isosbectic point around 580 nm.

For sodium assays the pH for optimal sensitivity is between 8.5 and 9.5 although sodium binding can be observed down to pH 5 and up to pH 11. To measure sodium in biological fluids, a suitable metal chelator or chelators will need to be added to bind metal ions other than sodium and prevent them from reacting with phosphonazo III. Phosphonazo III also binds potassium with about the same affinity and sensitivity it has for sodium. Therefore a suitable chelator is needed to prevent potassium binding to phosphonazo III. Lithium also binds to phosphonazo III and its binding characteristics are similar to sodium. Normally, lithium is not present in biological fluids unless the individual is on lithium therapy. Even in these individuals the therapeutic serum concentration would only be ~0.6 to 1.2 mmol/L (Fundamentals of Clinical Chemistry, 3ed., Norbert W. Tietz editor, p. 971) compared with a normal blood serum sodium concentration of 135 to 145 mmol/L. Thus lithium would not be expected to be a major interferrent. One could also add a lithium binding compound, e.g. dibenzyl-14-crown-4.

Examples of suitable heavy metal chelators to bind calcium, magnesium, iron, copper, zinc which are normally found in blood serum would be dicarboxylic acids, phosphonic acids, phosphoric acid, ethylenediaminetetraacetic acid (EDTA), ethylene glycol bis(2-aminoethyl ether)-N,N,N',N'-tetraacetic acid (EGTA), (1,2-Cyclohexylenedinitrilo) tetraacetic acid (CETA), diethylenetriaminepentaacetic acid (DTPA), citric acid nitrilotriacetic acid (NTA) O,O'-bis(2-aminoethyl)ethyleneblycol-N,N,N',N'-tetraacetic acid (GEDTA), iminodiacetic acid (IDA), N-(2-hydroxyethyl)iminodiacetic acid (HIDA) and N-(2-Hydroxyethyl)ethylenedianmine-N,N',N-triacetic acid (EDTA-OH) to name just a few. The heavy metal chelators can also serve as the buffer for the sodium assay. Effective concentrations of metal chelating agents would be about 0.0005 to 0.3 mol/L.

Potassium interference can be decreased by about 80% with the addition of crown ethers such as the 18-crown-6 in the presence of 50% dimethylsulfoxide. Fortunately, the potassium concentration in serum is only about 3.5 to 5 mmol/L compared to a normal sodium concentration of 135 to 145 mmol/L. Thus interference by potassium would be minor and could be prevented entirely by adding potassium to the sodium standard used to calibrate the assay.

It was discovered that the sensitivity of the complexation with sodium, potassium and lithium with phosphonazo III could be dramatically improved with addition of hygroscopic solvents or compounds to the phosphonazo III buffers. The improved sensitivity appears to be due in part to a suppression of the dissociation of the protons from the phosphonic and hydroxyl groups of phosphonazo III which has the effect of lowering the reagent absorbance at an alkaline pH. This in turn allows more phosphonazo III to be added to buffer which causes more sodium to be bound by the phosphonazo III. (See discussion below for theoretical basis for this observation).

A second reason for the enhanced sensitivity observed when hygroscopic solvents and compounds are added to the reagent may be due to the partial removal or complete removal of the hydration sphere surrounding sodium and other alkali metal ions. When an alkali metal ion, in this case sodium, is added to an aqueous solution it becomes immediately coordination by water molecules according to the following equation (1) (see *Advanced Inorganic Chemistry*, F. Albert Cotton ed., $2^{nd}$ edition 1967, Chapters 2 and 5). The coordination number, n, for sodium is believed to be 4 where 4 water molecules are tightly coordinated to sodium. With sodium this reaction is quite exothermic with 97 kcal/mol of energy given off. Before complexation with another ligand, L, can occur, where in this case the other ligand is phosphonazo III, the metal, sodium in this case, will have to first loose one or more of the tightly bound water molecules. This is illustrated in equations (2) and (3).

$$nH_2O + M^+ \rightleftharpoons M(H_2O)_j^+ + (n-j)H_2O \qquad (1)$$

$$M(H_2O)_j^+ \rightleftharpoons M(H_2O)_{j-k}^+ + kH_2O \qquad (2)$$

(where k=1 to 4)

$$M(H_2O)_{j-k}^+ + L^- \rightleftharpoons ML(H_2O)_{j-k} \qquad (3)$$

Thus any condition that would cause the removal or binding of water in the above will shift reaction (2) farther to the right which will in turn shift reaction (3) farther to the right with the net result that more of the metal ion will be bound by the ligand which in this case is phosphonazo III. This mechanism is also likely for the suppression of the ionization of phosphonazo III since the protons given up by phosphonazo III, $PH_6$, are hydrated by water molecules to form a hydronium ions as illustrated in equation (4). In this case removal of free water from the system would cause reaction (4) to be shifted to the left with less ionization of phosphonazo III at alkaline pH values and thus a lower absorbance.

$$PH_6 + nH_2O \rightleftharpoons PH_{6-x}^{x-} + (n-x)H_2O + xH_3O^+ \qquad (4)$$

(where x=1 to 6)

Several compounds were found to be useful as hygroscopic agents which increased the sensitivity of phosphonazo III in complex reactions with the alkali metals. A useful solvent which is very hygroscopic and found to significantly enhance sodium binding to phosphonazo III was dimethylsulfoxide (DMSO). It was effective over a wide pH range, from 5 to 11, and cold be used over a concentration range from 5% to 90% (volume dimethylsulfoxidetvolume buffer). Other classes of hygroscopic compounds found useful in increasing the sensitivity of sodium measurements with phosphonazo III were simple sugars, disaccharide, trisaccharides, polysaccharides and polyalcohols. Examples of these compounds would include glucose, galactose, lactose, maltose, maltotriose, dextran, mannitol and sorbitol. Also mixtures containing one or more of the hygroscopic compounds can added together to get an enhanced effect. For example, with 50% DMSO in the sodium reagent at pH 9 in 5 mmol/L DPTA buffer the increase in sensitivity was 4.1 fold compared to the same reagent without DMSO. When glucose was added to make a concentration of 25% the sensitivity was doubled again for an increase of 8.3 fold compared to the sensitivity in buffer only.

In general, for the hygroscopic compounds to be effective they need to be added in sufficient quantities to the buffer to cause a shift to the right in equations (2) and (3) and a shift to the left in equation (4). The net result is that more phosphonazo III can be added to the reagent and more of the alkali metal, sodium, in this case will be bound resulting in increased sensitivity. Typically to have a significant enhancement in sensitivity the buffer will need to contain at least about 5% by weight or volume of the hygroscopic compound. Any wavelength between about 500 and 700 nm can be used to measure the sodium-phosphonazo III complex. We have also observed that chlorophosphonazo III binds alkali ions under the same conditions as with phosphonazo III.

Turning now to some additional preferred aspects of the invention, there are provided some kits and methods measuring one of calcium, magnesium or sodium. It will be appreciated by those of ordinary skill that once the preferred kits have been described, use thereof in a colorimetric assay with known techniques and apparatus can be carried out without undue experimentation. For example, one diagnostic kit for specifically measuring calcium includes not only the phosphonazo III, but also:
a) one or more buffers selected from the group consisting of malonate, BES, DIPSO, MES, MOPS, MOPSO, BIS-TRIS, Imidazole, TES, ADA, ACES and TAPSO;
b) one or more a magnesium chelating agents selected from the group consisting of malonic acid, malonic acid salt, oxalic acid, oxalic acid salt, succinic acid, 8-hydroxyquinoline, phthalic acid, tartaric acid and phenylphosphonic acid;
c) about 10 to 200 umol/L phosphonazo III; and
d) the phosphonazo III is in a solution having a pH of about 3 to 10.

Within this aspect of this embodiment, some preferred amounts of above the call for:
a) about 0.08 mol/L malonic acid buffer;
b) about 83 umol/L phosphonazo III; and
c) the phosphonazo III being in a solution having a pH of about 5.5.

Another preferred diagnostic kit of the invention which is useful for measuring magnesium preferably includes the phosphonazo III along with:
a) one or more buffers selected from the group of BES, DIPSO, MES, MOPS, MOPSO, BIS-TRIS, Imidazole, TES, ADA, ACES and TAPSO;
b) a calcium chelating agent selected from the group consisting of EGTA;
c) 10 to 200 umol/L phosphonazo III; and
d) the phosphonazo III is in a solution having a pH of about 6.0 to 10.

Within this aspect of this embodiment, some preferred amounts of the call for:
a) about 0.05 mol/L DIPSO buffer;
b) about 6 mmol/L EGTA;
c) about 40 umol/L phosphonazo III; and
d) the phosphonazo III is in a solution having a pH of about 7.0.

Another preferred diagnostic kit of the invention which is useful for measuring sodium preferably includes the phosphonazo III along with:
a) one or more buffers selected from the group consisting of triethylamine, triethanolamine, diethanolamine, DTPA, CETA, EDTA, EGTA, EDTA-OH, HIDA, IDA, NTA and GEDTA;
b) one or more metal chelating compounds selected from the group consisting of DTPA, CETA, EDTA, EGTA, EDTA-OH, HIDA, IDA, NTA and GEDTA;
c) one or more potassium binding-compounds selected from the group consisting of 15-crown-5 and 18-crown-6;
d) 30 to 500 umol/L phosphonazo III;
e) one or more hygroscopic compounds selected from the group consisting of dimethylsulfoxide, glucose, maltose, lactose, sorbitol, mannitol, xylose and xylitol; and
f) the phosphonazo III is in a solution having a pH of about 5 to 11.

Within this aspect of this embodiment, some preferred amounts of the call for:
a) about 25 mmol/L DTPA;
b) about 4 mmol/L 18-crown-6;
c) about 200 umol/L phosphonazo III;
d) about 50% dimethylsulfoxide; and
e) the phosphonazo III is in a solution having a pH of about 9.

Calcium Assays

In the case of determining the amount of calcium in a sample, one preferred method include providing the preferred kit described above and then carrying out the steps of:
a) measuring the absorbance the reagent (reagent blank);
b) adding a sample containing calcium to the reagent;
c) measuring the absorbance after adding said sample to the reagent; and
d) subtracting the absorbance from step a) from step c) to obtain the absorbance change due to the calcium in the sample.

Another preferred method of determining the amount of calcium in a sample, includes:
a) providing a first reagent containing
  i) phosphonazo III;
  ii) a buffer selected from, for example, BES, DIPSO, MES, MOPS, MOPSO, BIS-TRIS, Imidazole, TES, ADA, ACES and TAPSO; and
  iii) a magnesium chelating agent selected from, for example, malonic acid, malonic acid salt, oxalic acid, oxalic acid salt, maleic acid, succinic acid, 8-hydroxyquinoline, phthalic acid, tartaric acid and phenylphosphonic acid;
b) adding a sample to a cuvet containing said first reagent and measuring the absorbance, reflectance or fluorescence thereof,
c) adding a second reagent containing a calcium chelator selected from, for example, EGTA to the cuvet of step b) and measuring the absorbance, reflectance or fluorescence thereof; and
d) subtracting the absorbance, reflectance or fluorescence obtained as a result of step c) from the absorbance, reflectance or fluorescence obtained as a result of step b) to obtain the net absorbance, reflectance or fluorescence due to calcium.

Yet another preferred method of determining the amount of calcium in a sample, includes:
a) providing a first reagent containing
  i) a buffer selected from, for example, BES, DIPSO, MES, MOPS, MOPSO, BIS-TRIS, Imidazole, TES, ADA, ACES and TAPSO; and
  ii) a magnesium chelator selected from, for example, malonic acid, malonic acid salt oxalic acid, oxalic acid salt, maleic acid, succinic acid, 8-hydroxyquinoline, phthalic acid, tartaric acid and phenylphosphonic acid;
b) adding a sample to a cuvet containing said first reagent and measuring the absorbance, reflectance or fluorescence thereof;
c) adding a second reagent containing phosphonazo III to the cuvet of step b) and measuring the absorbance, reflectance or fluorescence thereof; and
d) subtracting the absorbance, reflectance or fluorescence obtained as a result of step b) from the absorbance, reflectance or fluorescence obtained as a result of step c) to obtain the net absorbance, reflectance or fluorescence due to calcium.

A further preferred method of determining the amount of calcium in a sample, includes:
a) providing a first reagent containing a buffer selected from, for example, BES, DIPSO, MES, MOPS, MOPSO, BIS-TRIS, Imidazole, TES, ADA, ACES and TAPSO;
b) adding a sample to a cuvet containing said first reagent and measuring the absorbance, reflectance or fluorescence thereof;
c) adding a second reagent containing
   i) phosphonazo III; and
   ii) a magnesium chelating compound selected from, for example, malonic acid, malonic acid salt, oxalic acid, oxalic acid salt, maleic acid, succinic acid, 8-hydroxyquinoline, phthalic acid, tartaric acid and phenylphosphonic acid; to the cuvet of step b) and measuring the absorbance, reflectance or fluorescence thereof;
d) subtracting the absorbance, reflectance or fluorescence obtained as a result of step b) from the absorbance, reflectance or fluorescence obtained as a result of step c) to obtain the net absorbance, reflectance or fluorescence due to calcium.

A still further preferred method of determining the amount of calcium in a sample, includes:
a) providing a first reagent containing
   i) phosphonazo III; and
   ii) a buffer selected from, for example, BES, DIPSO, MES, MOPS, MOPSO, BIS-TRIS, Imidazole, TES, ADA, ACES and TAPSO;
b) adding a sample to a cuvet containing said first reagent and measuring the absorbance, reflectance or fluorescence thereof;
c) adding a second reagent containing a magnesium chelator selected from, for example, malonic acid, malonic acid salt, oxalic acid, oxalic acid salt, maleic acid, succinic acid, 8-hydroxyquinoline, phthalic acid, tartaric acid and phenylphosphonic acid to the cuvet of step b) and measuring the absorbance, reflectance or fluorescence thereof; and
d) subtracting the absorbance, reflectance or fluorescence obtained as a result of step c) from the absorbance, reflectance or fluorescence obtained as a result of step b) to obtain the net absorbance, reflectance or fluorescence due to calcium.

Magnesium Assays

In the case of determining the amount of magnesium in a sample, one preferred method includes providing the preferred kit described above and then carrying out the steps of:
a) measuring the absorbance of the reagent (reagent blank);
b) adding a sample containing magnesium to the reagent;
c) measuring the absorbance after adding said sample to the reagent; and
d) subtracting the absorbance from step a) from step c) to obtain the absorbance change due to the magnesium in the sample.

An alternative preferred method of determining the amount of magnesium in a sample, includes:
a) providing a first reagent containing
   i) phosphonazo III;
   ii) a buffer selected from, for example, BES, DIPSO, MES, MOPS, MOPSO, BIS-TRIS, Imidazole, TES, ADA, ACES, TAPSO; and
   ii) EGTA;
b) adding a sample to a cuvet containing said first reagent and measuring the absorbance, reflectance or fluorescence thereof;
c) adding a second reagent containing a chelator selected from the group consisting of EDTA, EDTA-OH, CETA, DTPA, HIDA, IDA GEDTA and NTA to the cuvet of step b) and measuring the absorbance, reflectance or fluorescence thereof; and
d) subtracting the absorbance, reflectance or fluorescence obtained as a result of step b) from the absorbance, reflectance or fluorescence obtained as a result of step c) to obtain the net absorbance, reflectance or fluorescence due to magnesium.

A further alternative preferred method of determining the amount of magnesium in a sample, includes:
a) providing a first reagent containing
   i) a buffer selected from, for example, BES, DIPSO,MES, MOPS, MOPSO, BIS-TRIS, Imidazole, TES, ADA, ACES and TAPSO; and
   ii) EGTA;
b) adding a sample to a cuvet containing said first reagent and measuring the absorbance, reflectance or fluorescence thereof;
c) adding a second reagent containing phosphonazo III to the cuvet of step b) and measuring the absorbance, reflectance or fluorescence thereof; and
d) subtracting the absorbance, reflectance or fluorescence obtained as a result of step b) from the absorbance, reflectance or fluorescence obtained as a result of step c) to obtain the net absorbance, reflectance or fluorescence due to magnesium.

Yet another preferred method of determining the amount of magnesium in a sample, includes:
a) providing a first reagent containing a buffer selected from, for example, the group consisting of BES, DIPSO, MES, MOPS, MOPSO, BIS-TRIS, Imidazole, TES, ADA, ACES and TAPSO;
b) adding a sample to a cuvet containing said first reagent and measuring the absorbance, reflectance or fluorescence thereof;
c) adding a second reagent containing
   i) phosphonazo III; and
   ii) EGTA;

to the cuvet of step b) and measuring the absorbance, reflectance or fluorescence thereof; and
d) subtracting the absorbance, reflectance or fluorescence obtained as a result of step b) from the absorbance, reflectance or fluorescence obtained as a result of step c) to obtain the net absorbance, reflectance or fluorescence due to magnesium.

A further preferred method of determining the amount of magnesium in a sample, includes:
a) providing a first reagent containing
   i) phosphonazo III and
   ii) a buffer selected from, for example, BES, DIPSO, MES, MOPS, MOPSO, BIS-TRIS, Imidazole, TES, ADA, ACES and TAPSO;
b) adding a sample to a cuvet containing said first reagent and measuring the absorbance, reflectance or fluorescence thereof;
c) adding a second reagent containing EGTA to the cuvet of step b) and measuring the absorbance, reflectance or fluorescence thereof; and
d) subtracting the absorbance, reflectance or fluorescence obtained as a result of step c) from the absorbance, reflectance or fluorescence obtained as a result of step b) to obtain the net absorbance, reflectance or fluorescence due to magnesium.

Sodium Assays

In the case of determining the amount of sodium in a sample, one preferred method includes providing the preferred kit described above containing phosphonazo III or a compound of formula 1 and then carrying out the steps of:
a) measuring the absorbance of the reagent (reagent blank);
b) adding a sample containing sodium to the reagent;
c) measuring the absorbance after adding said sample to the reagent; and
d) subtracting the absorbance from step a) from step c) to obtain the absorbance change due to the sodium in the sample.

In another embodiment of the invention, the measurement of the amount of sodium in a sample includes a two vial sodium reagent. The method of measuring sodium is made in an analogous manner as with the calcium reagent and magnesium reagents as above. In this case, the sodium buffer(s) are replaced by one or more of the following: dicarboxylic acids, phosphonic acids, phosphoric acid, ethylenediaminetetraacetic acid (EDTA), ethylene glycol bis(2-aminoethyl ether)-N,N,N',N'-tetraacetic acid (EGTA), (1,2-cyclohexylenedinitrilo)tetraacetic acid (CETA), dietylenetriaminepentaacetic acid (DTPA), citric acid nitrilotriacetic acid (NTA) O,O'-bis(2-aminoethyl) ethyleneblycol-N,N,N',N'-tetraacetic acid (GEDTA), iminodiacetic acid (IDA), N-(2-hydroxyethyl)iminodiacetic acid (HIDA) and N-(2-Hydroxyethyl)ethylenediamnrine-N,N',N-triacetic acid (EDTA-OH). The heavy metal chelating agent can also be selected from the above list of chelators and can also serve as the buffer(s). The heavy metal chelator could be present in either the first or second reagent. Also a potassium chelator, if deemed necessary, such as 18-crown-6 could be added to the first or second reagent. The hygroscopic compound(s) such as DMSO could added to either reagent one or reagent two, or, equally to both reagents.

In a two reagent sodium assay, analogous to measuring calcium and magnesium, a first absorbance reading would be made after sample and reagent one have been mixed. Then after adding reagent two a second absorbance reading would be made. From the absolute difference between the first and second absorbance readings, the absorbance due to the sodium in the sample can be determined using an appropriate sodium standard.

In each case, the methods of the invention are carried out by reading the absorbance over a wavelength of about 500 to 700 nm.

In those aspects of the invention where the compound of Formula (I) is chlorphosphonazo III, the diagnostic kit also includes about 25 mmol/L DTPA; about 4 mmol/L 18-crown-6; about 200 umol/L of chlorophosphonazo III; about 50% dimethylsulfoxide; and the chlorophosphonazo III is in a solution having a pH of about 9.

EXAMPLE 1

One Component Calcium Reagent

To 200 ml distilled water was dissolved 1.95 g MES and 0.252 g oxalic acid dihydrate. The pH (at 25° C.) was adjusted to 5.80 by addition of 2-amino-2-methyl-1-propanol. To 10 ml of this solution was added 0.6 mg phosphonazo III. The calcium assay was performed on a COBAS MIRA™ at 37° C. as follows. One hundred eighty uls of phosphonazo III reagent was pipetted into a MIRA cuvet. Fifty seconds later an absorbance reading was taken at 600 nm to measure the reagent blank absorbance. Two uls of an aqueous sample and 18 uls distilled water were added and after a 75 second incubation a final absorbance reading at 600 nm was taken. The net absorbance due to the calcium in the sample was determined by subtracting the initial absorbance reading from the final absorbance reading. The assay was calibrated using a 2.5 mmol/L calcium standard. Recoveries of calcium standards was as follows.

| Calcium Concentration in Sample (mmol/L) | Measured Calcium (mmol/L) |
|---|---|
| 1.0 | 1.0 |
| 2.0 | 2.1 |
| 3.0 | 3.0 |
| 4.0 | 3.8 |
| COBAS MIRA Factor | 7.09 |

With the above reagent a linearity to about 4.0 mmol/L is obtained. Clearly greater linearity can be obtained by increasing the phosphonazo III concentration and/or by reducing the sample volume. Additionally, it is apparent that wavelengths other than 600 nm can be used to measure calcium (see FIG. 1). The choice is left to the artisan as to which wavelength and the extent of linearity required for a particular need or application.

The addition of oxalic acid virtually eliminates magnesium interference up to 10 mmol/L using the above reagent and sample volumes. This is illustrated below where calcium samples with the indicated magnesium concentrations were present in the samples.

| Sample | | Measured Calcium | |
|---|---|---|---|
| Ca (mmol/L) | Mg (mmol/L) | (mmol/L) | % Recovery |
| 0 | 2.5 | 0.04 | 100 |
| 0 | 5.0 | 0.08 | 100 |
| 0 | 10.0 | 0.16 | 100 |
| 2.0 | 0 | 2.05 | 100 |
| 2.0 | 2.5 | 2.00 | 97.5 |
| 2.0 | 5.0 | 2.00 | 97.5 |
| 2.0 | 10.0 | 2.05 | 100 |

COBAS MIRA Factor 7.09

EXAMPLE 2

Two Reagent Calcium Assay

The calcium assay can also be run as a two reagent system e.g. if it is desirable to correct for the sample blank absorbance. For this method, several reagent configurations are possible. In one configuration, the phosphonazo III, with or without oxalate or other chelator if deemed necessary by the artisan, could be prepared in a concentrated form and added as a "Start Reagent." This reagent would be added to the "Primary Reagent" containing the sample and would be used for determining the absorbance due to the calcium in the sample. The Primary Reagent could simply be water or better a buffered solution at the desired pH of the calcium reaction with phosphonazo III. The Primary Reagent could also contain a chelator to prevent other metal ions from reacting with phosphonazo III. In still another two reagent method, phosphonazo III and oxalate could be in the Primary Reagent and the Start Reagent could contain an additional chelator(s). In this configuration, the chelator(s) in the Start Reagent would disrupt the calcium-phosphonazo III chelate thereby leaving only the absorbance due to the reagent and the sample. Examples of suitable chelators for inclusion in the Start Reagent could be EDTA, EGTA, CETA, DTPA, NTA, GEDTA, IDA, HIDA, EDTA-OH and citric acid. Suitable chelator concentrations is the Start Reagent would be about 1 to about 100 mmol/L. By subtracting the absorbance after the Start Reagent was added, from the absorbance before Start Reagent was added gives the net absorbance due to the calcium in the sample.

Primary Reagent in 0.05 mol/L MES buffer containing phosphonazo III and oxalate was prepared as described above. Start Reagent was prepared by adding 93.1 mg EDTA (disodium dihydrate salt) to ~9 ml distilled water, and after adjusting the pH to 5.8 with 2-amino-2-methyl-1-propanol was diluted to 10 ml with distilled wat The calcium assay was performed on a COBAS MIRA™ at 37° C. as follows. One hundred eighty uls of Primary Reagent and 2 uls sample followed with 8 uls distilled water was pipetted into a MIRA cuvet. About 10 seconds later an initial absorbance reading was taken at 600 nm. Twenty-five seconds later 20 uls of Start Reagent and 5 uls distilled water was added and after a 50 second incubation a final absorbance reading was taken at 600 nm. After subtracting the final absorbance reading from the initial absorbance the net absorbance due to the calcium in the sample was obtained. A 2.0 mmol/L calcium standard was used to calibrate the assay. Results were as follows.

| Sample | | Measured Calcium | |
|---|---|---|---|
| Ca (mmol/L) | Mg (mmol/L) | (mmol/L) | % Recovery |
| 1.0 | 0 | 1.01 | 100 |
| 2.0 | 0 | 1.97 | 100 |
| 3.0 | 0 | 2.98 | 100 |
| 4.0 | 0 | 4.03 | 100 |
| 1.0 | 10 | 1.11 | 110 |
| 2.0 | 10 | 2.14 | 109 |
| 3.0 | 10 | 3.05 | 102 |
| 4.0 | 10 | 3.91 | 97 |

COBAS CALCULATION Factor 7.24

The assay is linear to 4.0 mmol/L calcium with essentially no interference from magnesium.

EXAMPLE 3

One Component Calcium Assay

In this example the buffer not only maintains the pH but also serves as the chelator to prevent magnesium and other heavy metals from interfering in the measurement of calcium. To 400 ml distilled water was added 4.16 g malonic acid. The pH was adjusted to 5.5 with triethylamine and 250 mg sorbic acid was added and stirred until dissolved. To this solution was added 1.0 ml of Tergitol NP9 (Dow Chemical Co., Midland, Mich. 48678) and 1.5 ml COLADET ACS 1240 (Colonial Chemical, Inc., 225 Colonial Drive, South Pittsburg, Tenn. 37380) and 35 mg phosphonazo III. After diluting to 500 ml with distilled water the pH was adjusted to 5.5 at 25° C. with triethylamine. The calcium assay was performed on a COBAS MIRA™ at 37° C. as follows. Two hundred forty uls of phosphonazo III reagent was pipetted into a MIRA cuvet. Fifty seconds later an absorbance reading was taken at 600 nm to measure the reagent blank absorbance. Two uls of an aqueous calcium or magnesium sample and 10 uls distilled water were added and after a 75 second incubation a final absorbance reading at 600 nm was taken. The net absorbance due to the sample was determined by subtracting the initial absorbance reading from the final absorbance reading. The assay was calibrated using a 2.5 mmol/L (10 mg/dl) calcium standard. Recoveries of calcium standards were as follows.

| Sample | | Measured Calcium | |
|---|---|---|---|
| Ca (mg/dL) | Mg (mg/dL) | (mg/dL) | % Recovery |
| 5 | 0 | 4.9 | 98 |
| 7.5 | 0 | 7.5 | 100 |
| 10.0 | 0 | 10.2 | 102 |
| 15.0 | 0 | 15.3 | 102 |
| 20.0 | 0 | 20.3 | 102 |
| 0 | 24.7 (10 mmol/L) | 0.22 | less than 1% Mg interference |

COBAS MIRA Factor 32.7

EXAMPLE 4

One Component Magnesium Assay

To 200 mls distilled water was dissolved 2.43 g DIPSO [3-[N,N-Bis(hydroxyethyl)amino]-2-hydroxy-propane-sulfonic acid], 0.447 g EGTA and 8.2 mg phosphonazo III. The pH was adjusted to 7.0 (at 25° C.) with 2-amino-2-methyl-1-propanol. The magnesium assay was performed on a COBAS MIRA at 37° C. as follows. One hundred eighty uls of reagent was added to a MIRA cuvet and 50 seconds later an initial absorbance reading was taken at 600 nm to measure the reagent blank absorbance. Two uls of sample and 18 uls of distilled water were added and after a 75 second incubation a final absorbance at 600 nm was taken. After subtracting the initial absorbance reading from the final absorbance reading, the net absorbance due to the magnesium in the sample was calculated. The assay was calibrated using a 2.0 mmol/L magnesium standard. Results were as follows.

| Magnesium Concentration in Standard (mmol/L) | Measured Magnesium (mmol/L) | % Magnesium Recovery |
|---|---|---|
| 0.50 | 0.48 | 96 |
| 1.00 | 1.04 | 104 |
| 2.00 | 2.04 | 102 |
| 3.00 | 2.86 | 95 |

COBAS CALCULATION Factor 9.51

Thus with the above reagent, a linearity to about 3 mmol/L magnesium is obtained. Clearly increased linearity can be obtained by increasing the phosphonazo III concentration and/or by reducing the sample volume. Additionally, it is apparent that wavelengths other than 600 nm can be used to measure magnesium (see FIG. 1). The choice is left up to the artisan as to which length and the extent of linearity required for a particular need or application.

The addition of EGTA virtually eliminates calcium interference up to 4 mmol/L using the above sample and reagent volumes. This is illustrated in the table below where calcium at the indicated concentrations were present in 0.50 mmol/L magnesium samples.

| Sample | | Measured Magnesium | |
| --- | --- | --- | --- |
| Ca (mmol/L) | Mg (mmol/L) | (mmol/L) | % Recovery |
| 0 | 0.50 | 0.55 | 100 |
| 2.0 | 0.50 | 0.56 | 102 |
| 3.0 | 0.50 | 0.56 | 102 |
| 4.0 | 0.50 | 0.57 | 104 |

As with the calcium assay, it is apparent that the magnesium assay can also be ran as a two reagent configuration. In one configuration, for example, the sample could be added to the Primary Reagent which could consist of water or better a buffer with a calcium chelator(s) e.g. EGTA to complex calcium and other metal ions which may react with phosphonazo III. An absorbance reading would be taken to obtain the absorbance contribution of the sample. The Start Reagent would be added which contains phosphonazo III and a second absorbance reading would be taken. After subtracting the first absorbance reading from the second absorbance reading the net absorbance due to the magnesium in the sample is obtained. In another two reagent configuration Primary Reagent could consist of a buffer containing EGTA or other suitable calcium chelator and phosphonazo III to which the sample is added. The Start Reagent could consist of a buffered metal ion chelator(s) such as EDTA, CETA or DTPA. The chelator(s) in the second reagent would disrupt the magnesium-phosphonazo III complex leaving a solution with absorbances due to phosphonazo III plus the sample blank. By subtracting the second absorbance reading from the first absorbance reading the net absorbance due to the magnesium in the sample is obtained.

EXAMPLE 5

Two Vial Magnesium Reagent

A two vial magnesium reagent was prepared as follows. Primary Reagent was prepared as described above for a 1 vial magnesium reagent. Start Reagent was prepared by adding 37.2 mg disodium EDTA dihydrate to 9 mls distilled water and adjusting the pH at 25° C. to 7.0 with 2-amino-2-methyl-1-propanol and diluting to 10 mls with distilled water. The assay was performed on a COBAS MIRA™ at 37° C. as follows. One hundred eighty uls of Primary Reagent was pipetted into a MIRA cuvet. Twenty-five seconds later an initial absorbance reading was taken at 600 nm. Twenty uls of Start Reagent followed by 10 uls distilled water were added to the cuvet and after a 75 second incubation a final absorbance reading at 600 nm was taken. The net absorbance due to the magnesium in the sample was calculated by subtracting the final absorbance reading from the initial absorbance reading. The assay was calibrated with a 2.0 mmol/L magnesium standard. Results were as follows.

| Magnesium Concentration (mmol/L) in Sample | Measured Magnesium (mmol/L) | % Recovery |
| --- | --- | --- |
| 0.50 | 0.46 | 92 |
| 1.00 | 1.02 | 102 |
| 2.00 | 2.04 | 102 |
| 3.00 | 2.85 | 95 |

COBAS CALCULATION Factor 11.12

With the above reagent linearity to about 3.0 mmol/L is obtained. Clearly greater linearity can be obtained by increasing the phosphonazo III concentration or by also reducing the sample volume. Additionally, it is apparent that wavelengths other than 600 nm can be used to measure magnesium (see FIG. 1). The choice is left up to the artisan as to which wavelength and extent of linearity is required for a particular need or application.

When human serum samples were assayed for magnesium with an aqueous calibrator containing magnesium sulfate, a slight positive bias was observed compared with other magnesium methods. The positive bias was subsequently found to be due to a slight interference from sodium in the serum samples. Thus it would be recommended to use a serum calibrator when measuring magnesium in serum to overcome the slight sodium bias. Alternatively, a sodium chelator such as Kryptofix® could be added to the magnesium reagent to prevent sodium interference.

EXAMPLE 6

One vial Sodium Reagent

To 45 mls distilled water was added 0.938 g diethylenetriaminepentaacetic acid (DTPA). Triethylamine was added to adjust the pH to 9.5 and diluted to 50.0 ml with distilled water. To 1.5 ml of this solution was added 1.5 ml dimethylsulfoxide and phosphonazo III to make a 0.2 mmol/L solution. This solution was ran on a COBAS BIO at 37° C. (Roche Diagnostic Systems, Indianapolis Ind.) as follows. Two hundred uls of the phosphonazo III reagent were added to a cuvet and an absorbance reading taken at 650 nm to measure the absorbance of the reagent blank. About 2 minutes later 2 uls of an aqueous sodium sample and 4 uls distilled water were added. After a 90 second incubation a second absorbance reading was taken at 650 nm. By subtracting the first absorbance reading (reagent blank) from the second absorbance reading the absorbance due to the sodium in the sample can be determined. The assay was calibrated using a 140 mmol/L aqueous sodium standard.

| Sample (mmol/L Na) | Measured Sodium | % Recovery |
| --- | --- | --- |
| 120 | 120.1 | 100.1 |
| 140 | 140.5 | 100.4 |
| 160 | 157.8 | 98.6 |

The sodium test using phosphonazo III exhibits a linear response between a sodium concentration of 120 and 160 mmol/L. This range covers the expected serum sodium concentrations in a clinical population of samples.

Figure 2:
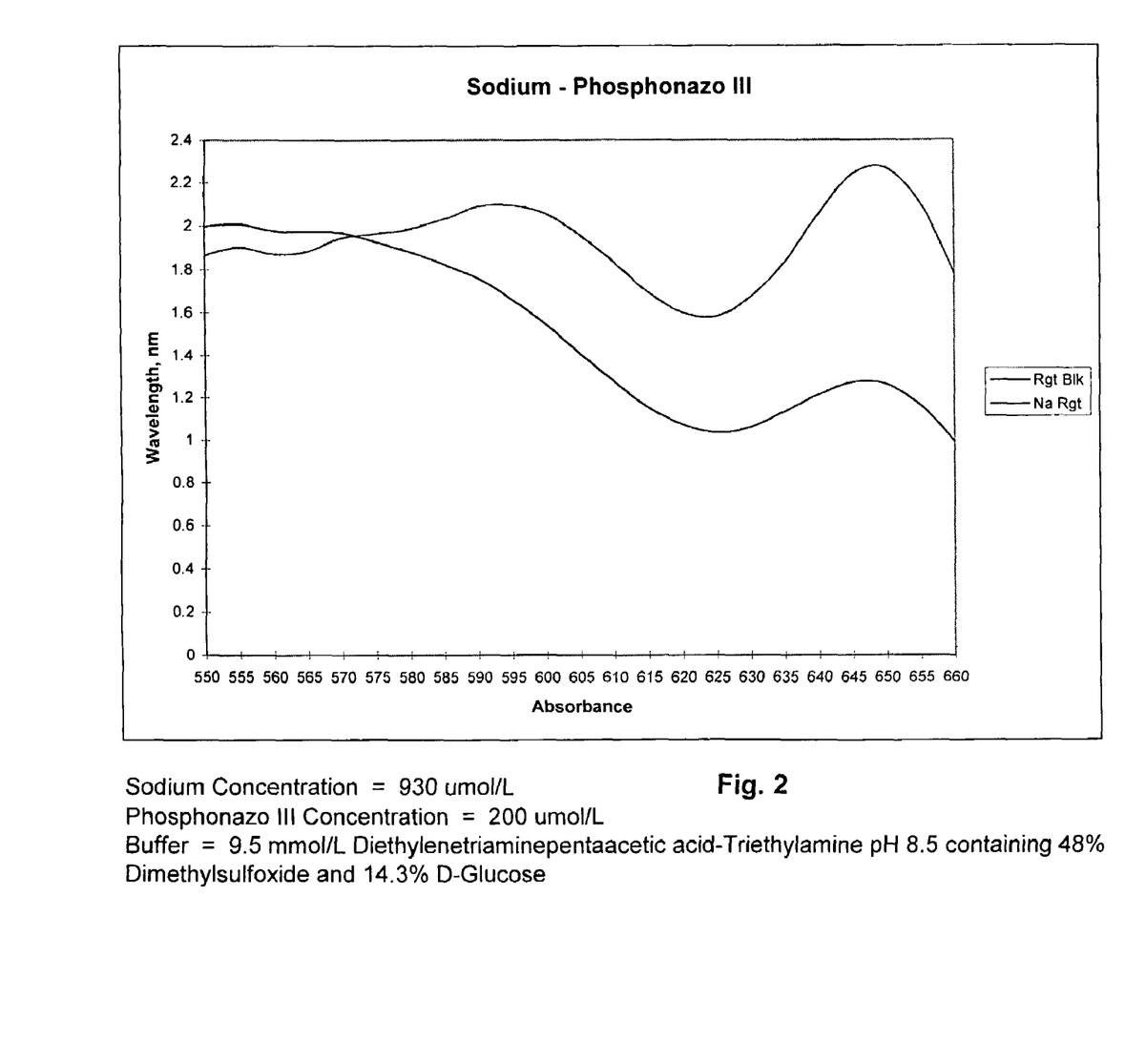
FIG. 2 shows the absorbance spectra of phosphonazo III and Na-phosphonazo III complex in 9.5 mmol/L dietylenetriaminepentaacetic acid-triethylamine buffer, pH 8.5 containing 48% dimethylsulfoxide and 14.3% D-glucose. The phosphonazo III concentration is 200 umol/L and the sodium concentration is 930 umol/L.

It is apparent that the sodium assay could also be configured as a two or more reagent system. In this case there are numerous possibilities as to which solutions the phosphonazo III, hygroscopic compound(s) and chelators and buffer(s) could be added. It is left up to artisan to determine which configuration is best for the particular application. Other wavelengths than 650 nm could also be used for measuring the sodium-phosphonazo III complex (see FIG. 2).

EXAMPLE 7

The procedure of Example 1 is repeated except that para-methoxyphosphonazo III, 0.6 mg, is used in place of the 0.6 mg phosphoazo III.

EXAMPLE 8

The procedure of Example 6 was repeated except that the reagent was made 200 umol/L chlorphophonazo III.

It is also apparent to those skilled in the art of diagnostic kit development that one may choose to add preservatives to the calcium, magnesium and sodium reagents to inhibit or prevent microbial growth. Also it may be advantageous for certain applications to add surfactants, detergents or wetting agents.

What is claimed:

1. A diagnostic reagent kit useful for the measurement of calcium, comprising:
   a) a compound of formula I:

wherein $R_1$, $R_2$, $R_3$, $R_4$, $R_5$, $R_6$, $R_7$, and $R_8$ are selected from the group consisting of H, $C_{1-6}$ alkyls, $C_{1-6}$ etheralkyls, $C_{1-6}$ branched alkyls, $C_{3-8}$ cycloalkyls and halogens;
   b) one or more magnesium chelating agents selected from the group consisting of malonic acid, malonic acid salt, oxalic acid, oxalic acid salt, succinic acid, 8-hydroxyquinoline, phthalic acid, tartaric acid and phenylphosphonic acid; and
   c) a buffer selected from the group consisting of malonate, BES, DIPSO, MES, MOPS, MOPSO, BIS-TRIS, Imidazole, TES, ADA, ACES and TAPSO.

2. The diagnostic reagent kit of claim 1, wherein the compound of formula I is

3. The diagnostic reagent kit of claim 2, wherein
   the concentration of phosphonazo III is about 10 to 200 umol/L; and
   the phosphonazo III is in a solution having a pH of about 3 to 10.

4. The diagnostic reagent kit of claim 3, comprising:
   a) about 0.08 mol/L malonic acid;
   b) about 83 umol/L phosphonazo III; and
   c) the phosphonazo III is in a solution having a pH of about 5.5.

5. A method for determining the presence of calcium in a sample, comprising:
   a) providing a diagnostic reagent kit of claim 4;
   b) measuring the absorbance of the reagent in said kit (reagent blank);
   c) adding a sample containing calcium to the reagent;
   d) measuring the absorbance after adding said sample to the reagent; and
   e) subtracting the absorbance from step b) from step d) to obtain the absorbance change due to the calcium in the sample.

6. The method of claim 5, where the absorbance is read over a wavelength of about 500 to 700 nm.

7. A method for determining the amount of calcium in a sample, comprising:
   a) providing a diagnostic reagent kit of claim 1;
   b) measuring the absorbance, reflectance or fluorescence of the reagent in said kit in step a) (reagent blank);
   c) adding a sample containing calcium to the reagent and thereafter measuring the absorbance, reflectance or fluorescence; and
   d) subtracting the absorbance, reflectance or fluorescence value obtained from step b) from the absorbance, reflectance or fluorescence value obtained from step c) to obtain the net absorbance, reflectance or fluorescence due to the calcium in the sample.

8. A diagnostic reagent kit useful for the measurement of magnesium, comprising a compound of the formula a) in a solution having a pH of about 7.0;
   b) about 0.05 mol/L DIPSO buffer;
   c) about 6 mmol/L EGTA; and
   d) about 10-200 umol/L phosphonazo III.

9. The diagnostic reagent kit of claim 8, comprising: about 40 umol/L phosphonazo III.

10. A method for determining the amount of magnesium in a sample, comprising:
    a) providing a diagnostic reagent kit of claim 8;
    b) measuring the absorbance, reflectance or fluorescence of the reagent in said kit in step a) (reagent blank);
    c) adding a sample containing magnesium to the reagent and thereafter measuring the absorbance, reflectance or fluorescence; and
    d) subtracting the absorbance, reflectance or fluorescence value obtained from step b) from the absorbance, reflectance or fluorescence value obtained from step c) to obtain the net absorbance, reflectance or fluorescence due to the magnesium in the sample.

11. The method of claim 10, where the absorbance is read over a wavelength of about 500 to 700 nm.

12. A diagnostic reagent kit useful for the measurement of sodium, comprising:
a) a compound of formula I:

wherein $R_1$, $R_2$, $R_3$, $R_4$, $R_5$, $R_6$, $R_7$, and $R_8$ are selected from the group consisting of H, $C_{1-6}$ alkyls, $C_{1-6}$ etheralkyls, $C_{1-6}$ branched alkyls, $C_{3-8}$ cycloalkyls and halogens;
b) one or more potassium chelating agents;
c) a buffer; and
d) a hygroscopic compound selected from the group consisting of dimethylsulfoxide, glucose, maltose, sucrose, sorbitol, mannitol, xylose and xylitol.

13. The diagnostic reagent kit of claim 12, wherein the compound of formula I is 14. The diagnostic reagent kit of claim 12, further comprising
a) one or more buffers selected from the group consisting of triethylamine, triethanolamine, diethanolamine, DTPA, CETA, EDTA, EGTA, EGTA-OH, HIDA, IDA, NTA and GEDTA;
b) one or more metal chelating compounds selected from the group consisting of DTPA, CETA, EDTA, EGTA, EDTA-OH, HIDA, IDA, NTA and GEDTA;
c) one or more potassium binding compounds selected from the group consisting of 15-crown-5 and 18-crown-6;
d) 30 to 500 umol/L phosphonazo III; and
e) the phosphonazo III is in a solution having a pH of about 5 to 11.

15. The diagnostic reagent kit of claim 14, comprising:
a) about 25 mmol/L DTPA;
b) about 4 mmol/L 18-crown-6;
c) about 200 umol/L phosphonazo III;
d) about 50% dimethylsulfoxide; and
e) the phosphonazo III is in a solution having a pH of about 9.

16. A method for determining the presence of sodium in a sample, comprising:
a) providing a diagnostic reagent kit of claim 15;
b) measuring the absorbance of the reagent in said kit (reagent blank);
c) adding a sample containing sodium to the reagent;
d) measuring the absorbance after adding said sample to the reagent; and
e) subtracting the absorbance from step b) from step d) to obtain the absorbance change due to the sodium in the sample.

17. The method of claim 16, where the absorbance is read over a wavelength of about 500 to 700 nm.

18. A method for determining the amount of sodium in a sample, comprising:
a) providing a diagnostic reagent kit of claim 12;
b) measuring the absorbance, reflectance or fluorescence of the reagent in said kit in step a) (reagent blank);
c) adding a sample containing sodium to the reagent and thereafter measuring the absorbance, reflectance or fluorescence; and
d) subtracting the absorbance, reflectance or fluorescence value obtained from step b) from the absorbance, reflectance or fluorescence value obtained from step c) to obtain the net absorbance, reflectance or fluorescence due to the sodium in the sample.

19. The diagnostic reagent kit of claim 12, wherein $R_3$ and $R_7$ are Cl.

20. The diagnostic reagent kit of claim 19, farther comprising:
a) about 25 mmol/L DTPA;
b) about 4 mmol/L 18-crown-6;
c) about 200 umol/L chlorophosphonazo III;
d) about 50% dimethylsulfoxide; and
e) the chlorophosphonazo III is in a solution having a pH of about 9.

21. A method for determining the presence of sodium in a sample, comprising:
a) providing a diagnostic reagent kit of claim 20;
b) measuring the absorbance the reagent in said kit (reagent blank);
c) adding a sample containing sodium to the reagent;
d) measuring the absorbance after adding said sample to the reagent; and
e) subtracting the absorbance from step b) from step d) to obtain the absorbance change due to the sodium in the sample.

22. The method of claim 21, where the absorbance is read over a wavelength of about 500 to 700 nm.

* * * * *

UNITED STATES PATENT AND TRADEMARK OFFICE
CERTIFICATE OF CORRECTION

PATENT NO.         : 7,288,414 B2
APPLICATION NO. : 11/109083
DATED              : October 30, 2007
INVENTOR(S)        : Richard A. Kaufman It is certified that error appears in the above-identified patent and that said Letters Patent is hereby corrected as shown below:

Column 3, lines 50-62, the chemical structure should appear as follows:

Column 4, lines 1-14, the chemical structure should appear as follows:

Column 19, lines 11-23 in Claim 1, the chemical structure should appear as follows:

:

UNITED STATES PATENT AND TRADEMARK OFFICE
CERTIFICATE OF CORRECTION

PATENT NO. : 7,288,414 B2
APPLICATION NO. : 11/109083
DATED : October 30, 2007
INVENTOR(S) : Richard A. Kaufman It is certified that error appears in the above-identified patent and that said Letters Patent is hereby corrected as shown below:

Column 19, lines 40-50 in Claim 2, the chemical structure should appear as follows:

Column 21, lines 5-14 in Claim 12, the chemical structure should appear as follows:

Column 21, lines 27-39 in Claim 13, the chemical structure should appear as follows:

UNITED STATES PATENT AND TRADEMARK OFFICE
CERTIFICATE OF CORRECTION

PATENT NO. : 7,288,414 B2
APPLICATION NO. : 11/109083
DATED : October 30, 2007
INVENTOR(S) : Richard A. Kaufman It is certified that error appears in the above-identified patent and that said Letters Patent is hereby corrected as shown below:

<u>Column 22, line 34-35 in Claim 20</u>, "farther comprising" should read --further comprising--.

Signed and Sealed this

Twenty-seventh Day of May, 2008

JON W. DUDAS
*Director of the United States Patent and Trademark Office*